(12) United States Patent
Bergins et al.

(10) Patent No.: US 10,196,574 B2
(45) Date of Patent: Feb. 5, 2019

(54) INDUSTRIAL PRODUCTION PLANT HAVING MINIMAL EMISSION OF GREENHOUSE GASES, IN PARTICULAR EMISSION OF CARBON DIOXIDE, AND METHOD FOR THE OPERATION THEREOF

(71) Applicant: Mitsubishi Hitachi Power Systems Europe GmbH, Duisburg (DE)

(72) Inventors: Christian Bergins, Datteln (DE); Torsten Buddenberg, Moers (DE); Efthymia-Ioanna Koytsoumpa, Duisburg (DE)

(73) Assignee: Mitsubishi Hitachi Power Systems Europe GmbH, Duisburg (DE)

( * ) Notice: Subject to any disclaimer, the term of this patent is extended or adjusted under 35 U.S.C. 154(b) by 0 days.

(21) Appl. No.: 15/508,080

(22) PCT Filed: Jul. 31, 2015

(86) PCT No.: PCT/EP2015/067708
§ 371 (c)(1),
(2) Date: Mar. 1, 2017

(87) PCT Pub. No.: WO2016/034344
PCT Pub. Date: Mar. 10, 2016

(65) Prior Publication Data
US 2017/0283724 A1      Oct. 5, 2017

(30) Foreign Application Priority Data
Sep. 1, 2014   (DE) .................. 10 2014 112 580

(51) Int. Cl.
*C10L 3/08* (2006.01)
*C07C 29/151* (2006.01)
(Continued)

(52) U.S. Cl.
CPC ............... *C10L 3/08* (2013.01); *B01J 19/245* (2013.01); *C07C 1/12* (2013.01); *C07C 29/1518* (2013.01);
(Continued)

(58) Field of Classification Search
CPC .. B01J 19/245; C25B 1/04; C10L 3/00; C10L 3/08; C07C 1/12; C07C 29/1518
See application file for complete search history.

(56) References Cited

U.S. PATENT DOCUMENTS

| 9,057,138 B2 | 6/2015 | Stuermer et al. |
| 2003/0022948 A1 | 1/2003 | Seiki et al. |

(Continued)

FOREIGN PATENT DOCUMENTS

| DE | 602 03 761 T2 | 3/2006 |
| DE | 10 2009 018 126 A1 | 10/2010 |

(Continued)

OTHER PUBLICATIONS

WO2013/029701, Ostsee Maritime GMBH (Inventor: Busse, K.H. et al.), Power Supply system, in Particular for the Field of Building Technology, English translation, 16 pages (Year: 2013).*

(Continued)

*Primary Examiner* — Yate' K Cutliff
(74) *Attorney, Agent, or Firm* — Cahn & Samuels, LLP

(57) ABSTRACT

The invention relates to an industrial production plant (1), which comprises a first production plant (2), which produces a $CO_2$-poor and $H_2$-rich exhaust gas from a carbon-containing feed material and which has an associated first exhaust-gas cleaning device (3) and an associated second exhaust-gas cleaning device (14). The problem addressed by the invention is that of creating a solution by means of which a carbon capture and utilization method can be effectively and efficiently performed. This problem is solved in that the (Continued)

industrial production plant (1) also comprises a gas-processing plant (4), which divides the exhaust gas into a carbon-containing, at least substantially $H_2$-free partial gas flow (6) and a carbon-free, $H_2$-rich partial gas flow (7); comprises an apparatus (19) for producing a $CO_2$-rich gas flow, to which apparatus at least a part of a $CO_2$-containing exhaust-gas flow (17) arising in a firing apparatus (11) can be fed after flowing through the second exhaust-gas cleaning device (14); and comprises a water electrolysis plant (24), which produces hydrogen ($H_2$) and oxygen ($O_2$), and a second production plant (20), which produces methanol and/or secondary methanol products and which has a $CO_2$ line connection (21) to the apparatus (19) on one side and an $H_2$ line connection (23) to the gas-processing plant (4) and the water electrolysis plant (24) on the other side.

20 Claims, 1 Drawing Sheet

(51) Int. Cl.
| | | |
|---|---|---|
| *C10L 3/00* | (2006.01) | |
| *B01J 19/24* | (2006.01) | |
| *C07C 1/12* | (2006.01) | |
| *C25B 1/04* | (2006.01) | |
| *C25B 9/06* | (2006.01) | |
| *C25B 15/00* | (2006.01) | |

(52) U.S. Cl.
CPC ............... *C10L 3/00* (2013.01); *C25B 1/04* (2013.01); *C25B 9/06* (2013.01); *C25B 15/00* (2013.01); *B01J 2219/24* (2013.01); *C10L 2290/38* (2013.01); *C10L 2290/42* (2013.01); *Y02E 60/366* (2013.01)

(56) References Cited

U.S. PATENT DOCUMENTS

| | | |
|---|---|---|
| 2011/0041740 A1 | 2/2011 | Reilly |
| 2011/0237839 A1 | 9/2011 | Waldstein |
| 2016/0153316 A1 | 6/2016 | Bergins et al. |

FOREIGN PATENT DOCUMENTS

| | | | |
|---|---|---|---|
| DE | 10 2014 103 311 A1 | 1/2015 | |
| EP | 1 205 532 A1 | 5/2002 | |
| FR | 2977089 A1 | 12/2012 | |
| WO | 2013/029701 A1 | 3/2013 | |
| WO | WO2013/029701 A1 * | 3/2013 | ............... C25B 1/04 |

OTHER PUBLICATIONS

Espacenet, English abstract for DE 602 03 761 T2, printed on Mar. 1, 2017.
Espacenet, English abstract for FR2977089A1, printed on Mar. 1, 2017.
European Patent Office, International Search Report for PCT/EP2015/067708, dated Oct. 28, 2015.

\* cited by examiner

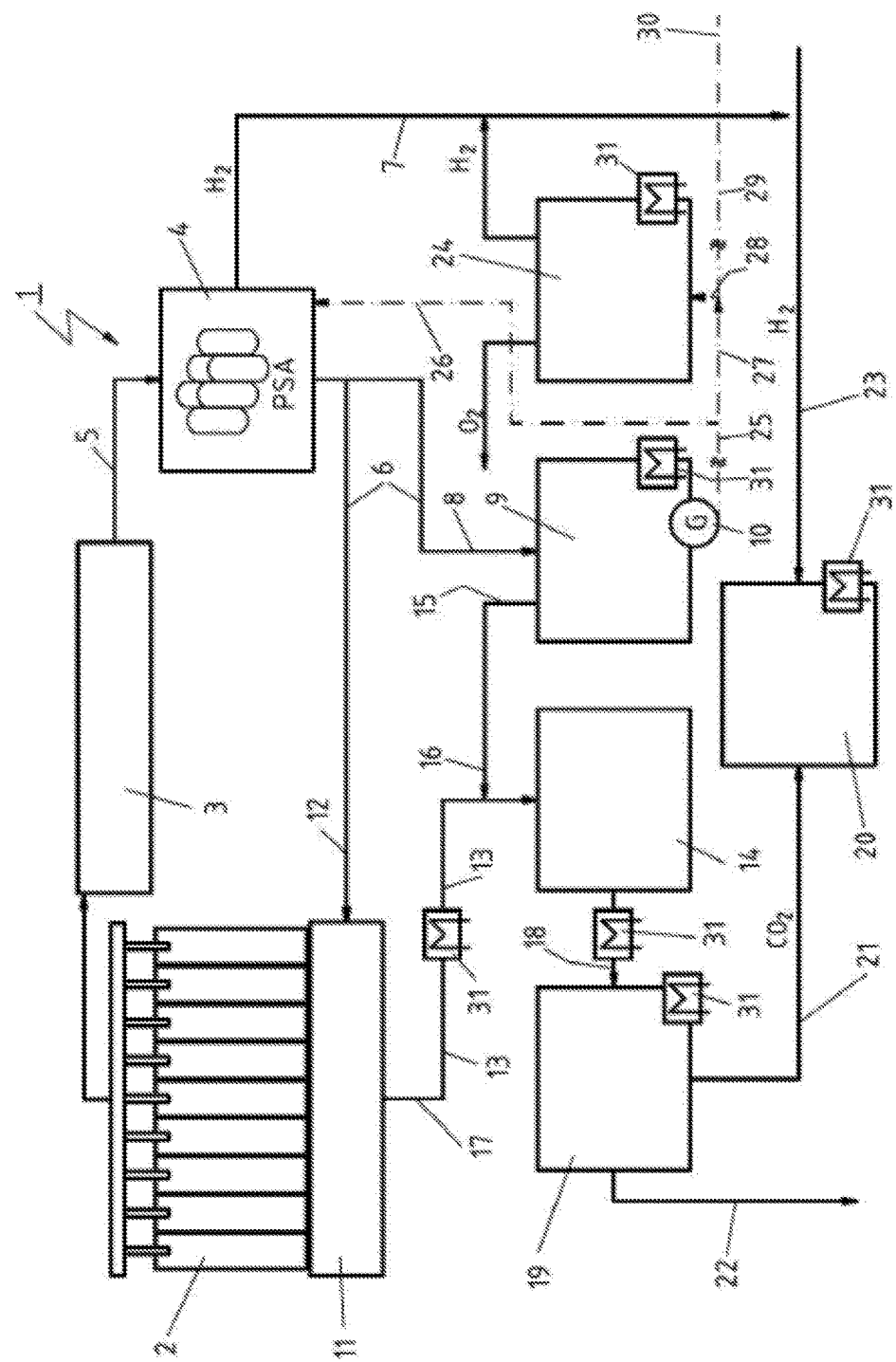

INDUSTRIAL PRODUCTION PLANT HAVING MINIMAL EMISSION OF GREENHOUSE GASES, IN PARTICULAR EMISSION OF CARBON DIOXIDE, AND METHOD FOR THE OPERATION THEREOF

This application is the National Stage of International Application No. PCT/EP2015/067708, filed on Jul. 31, 2015, which claims the benefit of German Application No. 10 2014 112 580.0 filed Sep. 1, 2014, which are hereby both incorporated by reference.

FIELD OF THE INVENTION

The invention is directed to an industrial production plant, in particular a coke oven, which comprises a first production plant producing a low-$CO_2$ and $H_2$-rich product gas or offgas from a carbon-containing feed with an associated first offgas purification apparatus and an associated second offgas purification apparatus.

Furthermore, the invention is directed to a method for the at least substantially $CO_2$-free operation of a first production plant producing a low-$CO_2$ and $H_2$-rich product gas or offgas from a carbon-containing feed with an associated first offgas purification apparatus and an associated second offgas purification apparatus.

BACKGROUND

It has been a long-standing general objective to operate industrial production plants with a very low emission of greenhouse gases, in particular a very low emission of $CO_2$. For this reason, a number of processes and apparatuses by means of which the respective greenhouse gas and in particular carbon dioxide can be filtered out from the offgas and stored have already been developed. These technologies, processes and apparatuses frequently subsumed under the collective term "carbon capture and storage" aim to remove carbon dioxide from an offgas, in particular a flue gas, and then store it. Since these removal processes all cause efficiency decreases or an increased capital outlay and thus incur associated additional costs, concepts which are subsumed under the term "carbon capture and utilization" and do not disclose the simple storage of the carbon dioxide but instead its further processing to give a saleable product have also already been published in the prior art. One such concept is, for example, the "power-to-fuel" concept in which the $CO_2$ in flue gases of power stations is converted with the aid of hydrogen ($H_2$) produced in an associated electrolysis of water into methane, methanol or downstream products of methane or methanol.

SUMMARY OF THE INVENTION

In the light of this background, it is an object of the invention to provide a solution which represents an advantageously implementable and easy-to-carry out alternative for an industrial production plant, by means of which a carbon capture and utilization process can be carried out effectively and efficiently.

The above object is achieved by an industrial production plant as disclosed herein.

The industrial production plant of the invention accordingly comprises a first production plant producing a low-$CO_2$ and $H_2$-rich product gas or offgas from a carbon-containing feed with an associated first offgas purification apparatus and an associated second offgas purification apparatus, a gas treatment plant which is connected to the first offgas purification apparatus via a first conduit connection and separates the product gas or offgas into a carbon-containing, at least substantially $H_2$-free gas substream and an at least substantially carbon-free, $H_2$-rich gas substream, where the substantially $H_2$-free gas substream can be fed at least partly by means of a second conduit connection to one or more firing device(s) present in the first production plant, a device for producing a $CO_2$-rich gas stream, into which at least part of the $CO_2$-containing offgas stream formed in the firing device(s) can be at least partly fed after flowing through the second offgas purification apparatus, a water electrolysis plant producing hydrogen ($H_2$) and oxygen ($O_2$) and a second production plant which produces methanol and/or downstream products of methanol and is firstly connected via the $CO_2$ conduit connection to the device producing the $CO_2$-rich gas stream and to which the $CO_2$-rich gas stream can be at least partly fed by means of this $CO_2$ conduit connection and, is secondly connected via the $H_2$-conduit connection to the gas treatment plant and the water electrolysis plant and into which the $H_2$-rich gas substream produced in the gas treatment plant and/or the hydrogen ($H_2$) produced in the water electrolysis plant can respectively be at least partly fed by means of this $H_2$ conduit connection.

The method of the invention for the at least substantially $CO_2$-free operation of a first production plant producing a low-$CO_2$ and $H_2$-rich product gas or offgas from a carbon-containing feed with an associated first offgas purification apparatus and an associated second offgas purification apparatus, in particular for the operation of an industrial production plant, is characterized in that the low-$CO_2$ and $H_2$-rich product gas or offgas is fed via a first conduit connection connected to the first offgas purification apparatus to a gas treatment plant which divides the product gas or offgas into a carbon-containing, at least substantially $H_2$-free gas substream and an at least substantially carbon-free, $H_2$-rich gas substream and the substantially $H_2$-free gas substream is at least partly fed via a second conduit connection to one or more firing device(s) of the first production plant, where at least part of the $CO_2$-containing offgas stream formed in the firing device(s) is, after passing through the second offgas purification apparatus, at least partly fed to a device for producing a $CO_2$-rich gas stream, where hydrogen ($H_2$) and oxygen ($O_2$) are produced by electrolysis of water in a water electrolysis plant and methanol and/or downstream products of methanol are produced in a second production plant and, firstly, the $CO_2$-rich gas stream produced in the device producing the $CO_2$-rich gas stream is at least partly fed to the second production plant and, secondly, the $H_2$-rich gas substream produced by the gas treatment plant and/or the hydrogen ($H_2$) produced in the water electrolysis plant is in each case at least partly fed via an $H_2$-conduit connection to the second production plant.

The industrial production plant of the invention and the method according to the invention offer the advantage that they allow 90% of the carbon dioxide produced in a first production plant producing a low-$CO_2$ and $H_2$-rich product gas or offgas from a carbon-containing feed, and also the total $CO_2$ formed in the industrial production plant, not to be discharged into the environment nor stored but instead to be converted directly into a commercial and saleable product, namely methanol or a downstream product of methanol. The direct production of the commercial product methanol or a downstream product of methanol improves the economics of such an industrial production plant. This is also contributed to by, inter alia, the fact that the "surplus power" which is at present frequently available in the public power grid as a result of over production by the power-producing generation plants based on renewable energies can be utilized for the envisaged electrolysis of water. Thus, a conventional power station, in particular a coal power station, can likewise be operated economically in the framework of this industrial production plant even in such cases, since the power which continues to arise in the minimum load region can be utilized in the electrolysis of water which can be run-up and run-down very flexibly in terms of time. Overall, an efficiency of 69% of the production plant can be achieved in the case of appropriate utilization and back-integration of waste heat arising in the production process possible in the industrial production plant of the invention.

In an embodiment of the industrial production plant, the invention therefore provides for it to comprise a power station which is fired using a carbon-containing fuel and has a water/steam circuit which comprises at least one steam-powered turbo set having at least one generator and is in media-conducting conduit connection with the gas treatment plant via a third conduit connection, by means of which the substantially $H_2$-free gas substream can be at least partly fed to the power station.

In an analogous way, the method of the invention is, in a further embodiment, characterized in that the substantially $H_2$-free gas substream is fed at least partly via a third conduit connection to a power station, where the power station has a water/steam circuit with at least one steam-powered turbo set with at least one generator and is fired using a carbon-containing fuel and the $CO_2$-containing offgas stream therefrom is at least partly fed to the associated second offgas purification apparatus.

In order to be able to utilize the flexibility of the power station and the flexible utilization of surplus power which may be present in the public power grid, the invention provides, in an advantageous embodiment, for the gas treatment plant and the water electrolysis plant to have an electrical connection both to the at least one generator of the power station and to the public power grid and optionally be able to be operated using electric power present in the public power grid, in particular surplus power, and/or using electric power generated by the at least one generator.

Owing to this crosslinking, firstly the power produced by the power station and secondly the power taken off from the grid, for example in the context of regulating a power station, can be flexibly distributed over the gas treatment plant and the water electrolysis and the water electrolysis can optionally be run-up or run-down for a short time.

Particularly when the first production plant producing a low-$CO_2$ and $H_2$-rich product gas or offgas from a carbon-containing feed has firing devices, as is the case for, for example, a coke oven, the gas substream produced in the gas treatment plant, which is at least substantially $H_2$-free and generally carbon-containing, can advantageously be burnt in such a firing plant. This applies particularly when this gas substream additionally contains an amount of methane, as is the case for a coke oven gas. The invention is therefore additionally characterized in that the one or more firing devices of the first production plant is/are, on the inlet side, in media-conducting conduit connection with the gas treatment plant via the second conduit connection and/or the third conduit connection, by means of which at least part of the carbon-containing, at least substantially $H_2$-free gas substream produced in the gas treatment plant can be fed as fuel to the firing device(s).

It is then also useful and particularly advantageous for the likewise $CO_2$-containing offgas formed, in particular, in such firing devices, for example in the firing device(s) of a coke oven, to be treated and utilized. In a further embodiment of the invention, the one or more firing devices of the first production plant is/are, therefore likewise on the offgas side, in media-conducting conduit connection via a fourth conduit connection with the second offgas purification apparatus and/or with a conduit connection conducting the $CO_2$-containing offgas stream of the power station, by means of which at least part of the $CO_2$-containing offgas streams, preferably all the $CO_2$-containing offgas streams, formed in the firing device(s) and/or the power station can be fed to the second offgas purification apparatus.

A particularly advantageous embodiment of a gas treatment plant is a pressure swing adsorption plant, so that the invention additionally provides, in a further embodiment, for the gas treatment plant to be configured as a pressure swing adsorption plant.

To be able to dissolve out the carbon dioxide from the product gas/offgas/flue gas stream formed and to be able to separate it from the latter, post combustion capture (PCC) processes have been found to be particularly advantageous. The invention is, in a further embodiment, therefore also characterized in that the device producing a $CO_2$-rich gas stream is configured as a post combustion capture (PCC) plant which scrubs out $CO_2$ from the $CO_2$-containing offgas stream of the power station and/or the one or more firing device(s) by means of an absorption medium.

The method of the invention can be advantageously employed in many industrial production plants. In particular, industrial production plants are advantageous, in which the first production plant producing a low-$CO_2$ and $H_2$-rich product gas or offgas from a carbon-containing feed is a coke oven producing a coke oven gas or a plant which gasifies or pyrolyzes or torrefies a carbon-containing starting material, which is likewise provided for by the invention.

The industrial production plant can be one of many production plants. In particular, in one embodiment of the invention, the industrial production plant comprises a smelting works and/or a steelworks or a cement works, in particular a rotary tube furnace, or one or more plants for producing molten glass or a chemical works or one or more paper production plants or is connected thereto by a conduit connection conveying a $CO_2$-containing gas stream.

In an advantageous embodiment of the method of the invention, the gas treatment plant and the water electrolysis plant have an electrical connection both to the at least one generator of the power station and to the public power grid and are optionally operated by means of power present in the public power grid, in particular surplus power, and/or using electric power produced by the at least one generator. This achieves the same advantage as indicated above for the industrial production plant, namely the flexible utilization of electric power produced or available from the public grid and associated flexibilization of power station operation.

In the method, too, it is advantageous for the first production plant producing a low-$CO_2$ and $H_2$-rich product gas or offgas to have one or more firing devices to which, on the inlet side, at least part of the carbon-containing, at least substantially $H_2$-free gas substream produced in the gas treatment plant is fed as fuel from the gas treatment plant and/or the second conduit connection.

Here too, the advantages indicated above for the industrial production plant are obtained in the same way.

Finally, this also applies to the further embodiment of the invention according to which the first production plant producing a low-$CO_2$ and $H_2$-rich product gas or offgas has one or more firing devices which is/are, on the offgas side, in media-conducting conduit connection via a fourth conduit connection with the second offgas purification apparatus and/or with a conduit connection conducting the $CO_2$-containing offgas stream of the power station, by means of which at least part of the $CO_2$-containing offgas streams, preferably all the $CO_2$-containing offgas streams, formed in the firing device(s) and/or the power station is fed to the second offgas purification apparatus.

BRIEF DESCRIPTION OF THE DRAWINGS

The invention is illustrated by way of example below with the aid of a drawing. FIG. 1 illustrates an industrial production plant according to the invention by means of which the method of the invention can be carried out.

DETAILED DESCRIPTION OF THE INVENTION

The industrial production plant designated overall by 1 in the single FIGURE comprises a first production plant 2 producing a low-$CO_2$ and $H_2$-rich product gas or offgas from a carbon-containing feed. In the example, the first production plant 2 is a coke oven, and the low-$CO_2$ and $H_2$-rich product gas or offgas produced therein is therefore a coke oven gas. Such a coke oven gas additionally has methane as constituent. The first production plant 2 is assigned a first offgas purification apparatus 3 into which the product gas or offgas produced in the first production plant 2 is fed. In this first offgas purification apparatus 3, the product gas or offgas, here coke oven gas, is purified to such an extent that it can be processed further in a downstream gas treatment plant 4. For this purpose, the product gas or offgas is generally subjected to dust removal and is optionally freed of acidic constituents in the first offgas purification apparatus 3. The product gas or offgas is fed to the gas treatment plant 4 via a first conduit connection 5 which is connected to the first offgas purification 3 and also to the gas treatment plant 4 in a media-conducting manner. In the gas treatment plant 4, the low-$CO_2$ and $H_2$-rich product gas stream or offgas stream fed in or the product or offgas is separated into a carbon-containing gas substream 6 which is at least substantially free of $H_2$ and a $H_2$-rich gas substream 7 which is at least substantially free of carbon. The gas treatment plant 4 is, in the example, a pressure swing adsorption plant as is adequately known from the prior art. The gas treatment plant 4 is in media-conducting conduit connection with a power station 9 via a third conduit connection 8, so that the at least substantially $H_2$-free and usually carbon-containing gas substream 6 produced in the gas treatment plant 4 can be at least partly fed to the power station and is fed thereto, in particular, to the burners to assist the combustion of fuel as fuel additive or fuel substitute, or is at least able to be fed in.

The power station 9 is a power station which is fired using a carbon-containing fuel, in particular gas or coal, and usually has a water/steam circuit which is not shown but comprises at least one steam-powered turbo set and at least one generator 10. However, biomass can also be used as carbon-containing fuel.

The first production plant 2 has a firing unit or firing device 11 in which at least part of the carbon-containing, at least substantially $H_2$-free gas substream 6 produced in the gas treatment plant 4 is burnt or used to assist combustion. For this purpose, the firing unit or firing device 11 is, on the inlet side, in media-conducting conduit connection via a second conduit connection 12 with the gas treatment plant 4 and/or the third conduit connection 8. Carbon-containing, at least substantially $H_2$-free gas substream 6 produced in the gas treatment plant 4 is advantageously fed to the firing device 11 in the amount required there for producing the necessary heat and firing power. Only the remaining part of the carbon-containing, at least substantially $H_2$-free gas substream 6 produced in the gas treatment plant 4 is then fed via the third conduit connection 8 to the power station 9.

On the offgas side, the firing device 11 of the first production plant 2 is in media-conducting conduit connection via a fourth conduit connection 13 conducting the $CO_2$-containing offgas stream 17 of the firing device 11 with a second offgas purification apparatus 14 to which the offgas formed in the firing device 11 is fed. Likewise, the second offgas purification apparatus 14 is in media-conducting conduit connection with the power station 9 via a conduit connection 16 conducting the $CO_2$-containing offgas stream 15 of the power station 9. In the second offgas purification apparatus 14, the $CO_2$-containing offgas streams 15 and 17 are freed of dust particles and largely of acidic constituents such as $SO_x$ and $NO_x$.

Via a fifth conduit connection 18, the $CO_2$-containing offgas stream which has been purified in this way is fed to a device 19 for producing a $CO_2$-rich gas stream. This device 19 is a post combustion capture (PCC) plant in which the $CO_2$ present in the offgas stream is scrubbed out from the $CO_2$-containing offgas stream 15 of the power station 9 and the $CO_2$-containing offgas stream 17 of the firing device 11 by means of an absorption medium when the streams flow through the second offgas purification apparatus 14.

The industrial production plant 1 further comprises a second production plant 20 producing methanol and/or downstream products of methanol to which the $CO_2$-rich gas stream produced in the device 19 producing the $CO_2$-rich gas stream is fed via a $CO_2$-conduit connection 21. The further gas stream which has been freed of the $CO_2$ leaves the device 19 as offgas 22.

The second production plant 20 producing methanol and/or downstream products of methanol is additionally in media-conducting conduit connection via an $H_2$-conduit connection 23 with the hydrogen-supplying site of a water electrolysis plant 24 producing hydrogen and oxygen and also with the side of the gas treatment plant 4 out of which the $H_2$-rich gas substream 7 flows, so that the hydrogen ($H_2$) produced in the water electrolysis plant 24 and/or the $H_2$-rich gas substream 7 produced in the gas treatment plant 4 can be at least partly fed to this second production plant 20. Methanol and/or one downstream product of methanol is produced as product in the second production plant 20 from the carbon dioxide ($CO_2$) and hydrogen ($H_2$) fed as starting materials to the second production plant 20 producing methanol and/or downstream products of methanol. The generator 10 of the power station 9, the gas treatment plant 4, the water electrolysis plant 24 and the pubic power grid 30 are switchably and controllably electrically connected to one another via an electrical connection 25, 26, 27, 28, 29. This makes it possible for the quantity of power available in each case, for example surplus power present in the public grid, to be utilized flexibly for the running-up or running-down of the gas treatment plant 4 and/or, in particular, the water electrolysis plant 24. Likewise, the power station 9 can be kept at such a high power level that economical operation is possible, since methanol or a downstream product of methanol is always produced as coproduct and the power station power used is not utilized solely to produce electric power for the pubic grid or the apparatuses, devices or plants hitherto present in a respective industrial production plant.

In the device 19 for producing a $CO_2$-rich gas stream, up to 90% of the carbon dioxide fed in via the fifth conduit connection 18 can be separated off from the gas stream fed in and fed into the $CO_2$-conduit connection 21.

Apart from the hydrogen ($H_2$) produced in the water electrolysis plant 24, the oxygen ($O_2$) produced there can also be passed to a further use. It can be used as oxidant in the combustion of fuel in the power station 9 or in other plants of the industrial production plant 1.

The hydrogen ($H_2$) formed as substantially carbon-free, $H_2$-rich gas substream 7 in the gas treatment plant 4 configured as pressure swing adsorption plant and likewise the hydrogen ($H_2$) formed in the water electrolysis plant 24 are conditioned in the usual way and mixed with the pressurized carbon dioxide ($CO_2$) originating from the device 19 for producing a $CO_2$-rich gas stream and reacted stoichiometrically with the introduced carbon dioxide ($CO_2$) in the second production plant 20 to form methanol and/or downstream products of methanol.

When the device 19 is configured as PCC plant which scrubs out $CO_2$ from the $CO_2$-containing offgas stream 15 of the power station 9 and/or the $CO_2$-containing offgas stream 17 of the one or more firing device(s) 11 by means of an absorption medium, an amine or an amine solution is advantageously used as scrubbing medium or absorption medium.

To allow good utilization of production heat or waste heat which arises and to be able to realize heat transfers and/or back-integrations of heat into various places in the industrial production plant 1, the various conduits or devices in the industrial production plant 1 are each provided with assigned heat exchangers or heat transfer systems which are uniformly denoted by the reference numeral 31.

In an example of a coke oven as first production plant 2 producing a low-$CO_2$ and $H_2$-rich product gas or offgas from a carbon-containing feed and having a capacity of about 1 630 000 metric tons of coke/year, part of the coke oven gas or coking applied gas produced is used for firing the firing devices 11 necessary for the coke oven. The amount of coke oven gas formed at this total production of coke is 394 $MW_{th}$ or 9.87 kg/s, of which 175.62 MWth or 4.4 kg/s are used for the firing device(s) 11 and the remainder is fed to the power station 9. The $CO_2$ emission of the firing device(s) 11 is then 6.75 kg/s and that of the power station is 8.14 kg/s.

After passing through the first offgas purification apparatus 3, the product gas or offgas comprises 23.04% by volume of $CH_4$, 2.69% by volume of other hydrocarbons, 59.53% by volume of $H_2$, 0.96% by volume of $CO_2$, 3.84% by volume of CO, 0.19% by volume of $O_2$, 5.76% by volume of $N_2$ and 3.98% by volume of $H_2O$.

In the gas treatment plant 4, about 94% of the hydrogen ($H_2$) is separated off as $H_2$-rich gas substream 7 from this low-$CO_2$ and $H_2$-rich product gas or offgas fed in. The remaining substantially $H_2$-free gas substream 6 has a composition of 52.33% by volume of $CH_4$, 6.11% by volume of other hydrocarbons, 8.11% by volume of $H_2$, 2.18% by volume of $CO_2$, 8.72% by volume of CO, 0.43% by volume of $O_2$, 13.08% by volume of $N_2$ and 9.04% by volume of $H_2O$. It flows at a mass flow of 8.74 kg/s and has a calorific value of 29.58 kJ/kg. This substantially $H_2$-free substream 6 is partly fed to the firing device 11, which requires a mass flow of 5.94 kg/s or 175.62 $MW_{th}$ and produces an offgas mass flow of $CO_2$-containing offgas stream 17 of 10.12 kg/s of $CO_2$, which is fed together with the $CO_2$-containing offgas stream 15 of the power station 9 to the second offgas purification apparatus 14. 82.8 $MW_{th}$ are fed as remaining substantially $H_2$-free gas substream 6 to the power station 9, with the power station 9 producing a mass flow of 4.77 kg/s of $CO_2$. In the PCC plant 19, 90% of the $CO_2$ fed in and thus 90% of the total $CO_2$ produced in the industrial production plant 1 is scrubbed out from the gas stream by means of an amine solution and converted into a $CO_2$-rich gas stream. This $CO_2$-rich gas stream obtained is pressurized and fed, like the hydrogen ($H_2$) obtained as $H_2$-rich gas substream 7 from the gas treatment plant 4 and the hydrogen ($H_2$) obtained in the water electrolysis plant 24 to the second production plant 20 producing methanol and/or downstream products of methanol. The gas treatment plant 4 produces an $H_2$-rich gas substream 7 having a mass flow of 1.13 kg/s or 135.45 $MW_{th}$ of hydrogen ($H_2$) and the water electrolysis plant 24 produces, at an input of 62 $MW_e$, a mass flow of 1.526 kg/s, so that a production of 29.15 metric tons of methanol/hour is obtained under stoichiometric conditions in the second production plant 20.

In the case of a 14 $MW_e$ pressure swing adsorption plant 4 and without offgas heat utilization, this process according to the invention or this example of the method of the invention has an efficiency of 69%, while conventional plants which provide merely for combustion of the coke oven gas in the power station 9 and do not comprise any methanol production or any electrolysis of water have an efficiency of only 42%.

The invention claimed is:

1. An industrial production plant comprising:
    a first production plant producing a low-$CO_2$ and $H_2$-rich product gas or offgas from a carbon-containing feed with an associated first offgas purification apparatus and an associated second offgas purification apparatus;
    a gas treatment plant which is connected to the first offgas purification apparatus via a first conduit connection and separates the low-$CO_2$ and $H_2$-rich product gas or offgas into a carbon-containing, at least substantially $H_2$-free gas substream and an at least substantially carbon-free, $H_2$-rich gas substream, where the substantially $H_2$-free gas substream can be fed at least partly by means of a second conduit connection to one or more firing device(s) present in the first production plant;
    a device for producing a $CO_2$-rich gas stream, into which at least part of $CO_2$-containing offgas stream formed in the firing device(s) can be at least partly fed after flowing through the second offgas purification apparatus; and
    a water electrolysis plant producing hydrogen ($H_2$) and oxygen ($O_2$) and a second production plant which produces methanol and/or downstream products of methanol and is firstly connected via a $CO_2$ conduit connection to the device producing the $CO_2$-rich gas stream and to which the $CO_2$-rich gas stream can be at least partly fed by means of this $CO_2$ conduit connection and, is secondly connected via a $H_2$-conduit connection to the gas treatment plant and the water electrolysis plant and into which the $H_2$-rich gas substream produced in the gas treatment plant and/or the hydrogen ($H_2$) produced in the water electrolysis plant can respectively be at least partly fed by means of this $H_2$ conduit connection.

2. The industrial production plant as claimed in claim 1, further comprising:

a power station which is fired using a carbon-containing fuel and has a water/steam circuit which includes at least one steam-powered turbo set having at least one generator and is in media-conducting conduit connection with the gas treatment plant via a third conduit connection, by means of which the substantially $H_2$-free gas substream can be at least partly fed to the power station.

3. The industrial production plant as claimed in claim 2, wherein the gas treatment plant and the water electrolysis plant have an electrical connection both to the at least one generator of the power station and to a public power grid.

4. The industrial production plant as claimed in claim 3, wherein the one or more firing device(s) of the first production plant is/are, on an inlet side, in media-conducting conduit connection with the gas treatment plant via the second conduit connection and/or the third conduit connection, by means of which at least part of the carbon-containing, at least substantially $H_2$-free gas substream produced in the gas treatment plant can be fed as fuel to the firing device(s).

5. The industrial production plant as claimed in claim 1, wherein the one or more firing device(s) of the first production plant is/are, on an offgas side, in media-conducting conduit connection via a fourth conduit connection with the second offgas purification apparatus and/or with a conduit connection conducting the $CO_2$-containing offgas stream of the power station, by means of which at least part of $CO_2$-containing offgas streams or substantially all the $CO_2$-containing gas streams, formed in the firing device(s) and/or the power station can be fed to the second offgas purification apparatus.

6. The industrial production plant as claimed in claim 4, wherein the gas treatment plant is configured as a pressure swing adsorption plant.

7. The industrial production plant as claimed in claim 4, wherein the device producing a $CO_2$-rich gas stream is configured as a post combustion capture (PCC) plant which scrubs out $CO_2$ from the $CO_2$-containing offgas stream of the power station and/or the one or more firing device(s) by an absorption medium.

8. The industrial production plant as claimed in claim 1, wherein the first production plant producing a low-$CO_2$ and $H_2$-rich product gas or offgas from a carbon-containing feed is a coke oven producing a coke oven gas or a plant which gasifies or pyrolyzes or torrefies a carbon-containing starting material.

9. The industrial production plant as claimed in claim 1, further comprising:
a smelting works, a steelworks, a cement works, a rotary tube furnace, one or more plants for producing molten glass or a chemical works, or one or more paper production plants or is connected thereto by a conduit connection conveying a $CO_2$-containing gas stream.

10. A method for the at least substantially $CO_2$-free operation of a first production plant producing a low-$CO_2$ and $H_2$-rich product gas or offgas from a carbon-containing feed with an associated first offgas purification apparatus and an associated second offgas purification apparatus, the method comprising:
feeding the low-$CO_2$ and $H_2$-rich product gas or offgas via a first conduit connection connected to the first offgas purification apparatus to a gas treatment plant;
dividing the low-$CO_2$ and $H_2$-rich product gas or offgas into a carbon-containing, at least substantially $H_2$-free gas substream and an at least substantially carbon-free, $H_2$-rich gas substream by the gas treatment plant;
feeding the substantially $H_2$-free gas substream at least partly via a second conduit connection to one or more firing device(s) of the first production plant,
where at least part of $CO_2$-containing offgas stream formed in the firing device(s) is, after passing through the second offgas purification apparatus, at least partly fed to a device for producing a $CO_2$-rich gas stream;
producing hydrogen ($H_2$) and oxygen ($O_2$) by electrolysis of water in a water electrolysis plant;
producing methanol and/or downstream products of methanol in a second production plant and, firstly,
feeding the $CO_2$-rich gas stream produced in the device producing the $CO_2$-rich gas stream at least partly to the second production plant and, secondly,
feeding the $H_2$-rich gas substream produced by the gas treatment plant and/or the hydrogen ($H_2$) produced in the water electrolysis plant in each case at least partly via an $H_2$-conduit connection to the second production plant.

11. The method as claimed in claim 10, wherein the substantially $H_2$-free gas substream is fed at least partly via a third conduit connection to a power station, where the power station has a water/steam circuit with at least one steam-powered turbo set with at least one generator and is fired using a carbon-containing fuel and a $CO_2$-containing offgas stream therefrom is at least partly fed to the associated second offgas purification apparatus.

12. The method as claimed in claim 11, wherein the gas treatment plant and the water electrolysis plant have an electrical connection both to the at least one generator of the power station and to a public power grid and are optionally operated by means of power present in the public power grid, surplus power, and/or using electric power produced by the at least one generator.

13. The method as claimed in claim 12, wherein the first production plant producing a low-$CO_2$ and $H_2$-rich product gas or offgas has one or more firing devices to which, on an inlet side, at least part of the carbon-containing, at least substantially $H_2$-free gas substream is fed as fuel from the gas treatment plant and/or the third conduit connection.

14. The method as claimed in claim 13, wherein the first production plant producing a low-$CO_2$ and $H_2$-rich product gas or offgas has one or more firing devices which is/are, on an offgas side, in media-conducting conduit connection via a fourth conduit connection with the second offgas purification apparatus and/or with a conduit connection conducting the $CO_2$-containing offgas stream of the power station, by means of which at least part of $CO_2$-containing offgas streams or all the $CO_2$-containing offgas stream, formed in the firing device(s) and/or the power station is fed to the second offgas purification apparatus.

15. The method as claimed in claim 10, wherein the first production plant producing a low-$CO_2$ and $H_2$-rich product gas or offgas has one or more firing devices to which, on an inlet side, at least part of the carbon-containing, at least substantially $H_2$-free gas substream is fed as fuel from the gas treatment plant and/or a third conduit connection.

16. The method as claimed in claim 10, wherein the first production plant producing a low-$CO_2$ and $H_2$-rich product gas or offgas has one or more firing devices which is/are, on an offgas side, in media-conducting conduit connection via a fourth conduit connection with the second offgas purification apparatus and/or with a conduit connection conducting a $CO_2$-containing offgas stream of a power station, by means of which at least part of $CO_2$-containing offgas streams or all the $CO_2$-containing offgas streams, formed in the firing device(s) and/or the power station is fed to the second offgas purification apparatus.

17. The industrial production plant as claimed in claim 2, wherein the gas treatment plant and the water electrolysis plant have an electrical connection both to the at least one generator of the power station and to a public power grid and is operated using power present in the public power grid and/or using electric power generated by the at least one generator.

18. The industrial production plant as claimed in claim 1, wherein the one or more firing device(s) of the first production plant is/are, on an inlet side, in media-conducting conduit connection with the gas treatment plant via the second conduit connection and/or a third conduit connection, by means of which at least part of the carbon-containing, at least substantially $H_2$-free gas substream produced in the gas treatment plant can be fed as fuel to the firing device(s).

19. The industrial production plant as claimed in claim 1, wherein the gas treatment plant is configured as a pressure swing adsorption plant.

20. The industrial production plant as claimed in claim 1, wherein the device producing a $CO_2$-rich gas stream is configured as a post combustion capture (PCC) plant which scrubs out $CO_2$ from the $CO_2$-containing offgas stream of a power station and/or the one or more firing device(s) by an absorption medium.

\* \* \* \* \*